(12) United States Patent
Behravesh et al.

(10) Patent No.: US 7,720,533 B2
(45) Date of Patent: May 18, 2010

(54) APPARATUS AND METHOD FOR DELIVERING A BIOCOMPATIBLE MATERIAL TO A SURGICAL SITE

(75) Inventors: Essy Behravesh, Decatur, GA (US); Jian Q. Yao, Austin, TX (US); Xiao Huang, Austin, TX (US); Victor Zaporojan, Austin, TX (US); Jizong Gao, Cedar Park, TX (US)

(73) Assignee: Zimmer Orthobiologicals, Inc., Austin, TX (US)

( * ) Notice: Subject to any disclaimer, the term of this patent is extended or adjusted under 35 U.S.C. 154(b) by 230 days.

(21) Appl. No.: 11/613,456

(22) Filed: Dec. 20, 2006

(65) Prior Publication Data

US 2008/0154234 A1 Jun. 26, 2008

(51) Int. Cl.
 *A61N 1/30* (2006.01)
(52) U.S. Cl. .................. 604/20; 604/21; 604/264
(58) Field of Classification Search ............. 604/20, 604/21, 113, 114, 191, 264
See application file for complete search history.

(56) References Cited

U.S. PATENT DOCUMENTS

| | | | |
|---|---|---|---|
| 5,069,881 A | 12/1991 | Clarkin | |
| 5,410,016 A | 4/1995 | Hubbell et al. | |
| 5,443,454 A * | 8/1995 | Tanabe et al. | 604/264 |
| 5,556,429 A * | 9/1996 | Felt | 128/898 |
| 5,669,544 A | 9/1997 | Schulze et al. | |
| 5,673,840 A | 10/1997 | Schulze et al. | |
| 5,673,841 A | 10/1997 | Schulze et al. | |
| 5,680,982 A | 10/1997 | Schulze et al. | |
| 5,692,668 A | 12/1997 | Schulze et al. | |
| 5,709,854 A | 1/1998 | Griffith-Cima et al. | |
| 5,749,968 A | 5/1998 | Melanson et al. | |
| 5,826,776 A | 10/1998 | Schulze et al. | |
| 5,866,630 A | 2/1999 | Mitra et al. | |
| 5,876,208 A | 3/1999 | Mitra et al. | |
| 5,888,491 A | 3/1999 | Mitra et al. | |
| 6,022,361 A | 2/2000 | Epstein et al. | |
| 6,143,214 A | 11/2000 | Barlow | |
| 6,271,320 B1 | 8/2001 | Keller et al. | |

(Continued)

FOREIGN PATENT DOCUMENTS

WO 0006216 2/2000

(Continued)

*Primary Examiner*—Kevin C Sirmons
*Assistant Examiner*—Bhisma Mehta
(74) *Attorney, Agent, or Firm*—Howrey LLP

(57) ABSTRACT

A device for delivering a biocompatible material to a surgical site includes a cannula having proximal and distal portions and at least a first interior lumen disposed therebetween through which the biocompatible material is delivered. The device further includes an initiation member for initiating cross-linking of the biocompatible material while the biocompatible material is within the cannula. The cannula may include a heating element to thermally initiate cross-linking. Alternately, the cannula may include a second lumen for transmitting light from a light source. A movable blocking element controls the amount of light that passes into the first lumen. A method of delivering a curable biocompatible material to a surgical site includes positioning a distal portion of a cannula adjacent the surgical site and introducing the biocompatible material through a first lumen of the cannula. Cross-linking of the biocompatible material is then initiated while the biocompatible material is within the cannula.

14 Claims, 3 Drawing Sheets

U.S. PATENT DOCUMENTS

| | | |
|---|---|---|
| 6,312,668 B2 | 11/2001 | Mitra et al. |
| 6,338,878 B1 | 1/2002 | Overton et al. |
| 6,370,920 B1 | 4/2002 | Overton et al. |
| 6,425,704 B2 | 7/2002 | Voiers et al. |
| 6,534,591 B2 | 3/2003 | Rhee et al. |
| 6,652,883 B2 | 11/2003 | Goupil et al. |
| 6,676,971 B2 | 1/2004 | Goupil et al. |
| 6,697,143 B2 | 2/2004 | Freeman |
| 6,705,790 B2 | 3/2004 | Quintero et al. |
| 6,713,772 B2 | 3/2004 | Goodman et al. |
| 6,800,663 B2 | 10/2004 | Asgarzadeh et al. |
| 6,818,008 B1 | 11/2004 | Cates et al. |
| 2002/0064512 A1 | 5/2002 | Petersen et al. |
| 2002/0150550 A1 | 10/2002 | Petersen |
| 2002/0198599 A1 | 12/2002 | Haldimann |
| 2003/0065389 A1 | 4/2003 | Petersen |
| 2003/0077244 A1 | 4/2003 | Petersen |
| 2003/0134032 A1 | 7/2003 | Chaouk et al. |
| 2003/0176602 A1 | 9/2003 | Schmidt et al. |
| 2003/0211073 A1 | 11/2003 | Goupil et al. |
| 2003/0223956 A1 | 12/2003 | Goupil et al. |
| 2004/0230309 A1 | 11/2004 | DiMauro et al. |
| 2005/0129656 A1 | 6/2005 | Goupil et al. |
| 2005/0175704 A1 | 8/2005 | Petersen |
| 2005/0209601 A1 | 9/2005 | Bowman et al. |
| 2005/0209602 A1 | 9/2005 | Bowman et al. |
| 2005/0287218 A1 | 12/2005 | Chaouk et al. |

FOREIGN PATENT DOCUMENTS

| | | |
|---|---|---|
| WO | 0048837 | 8/2000 |
| WO | 0062832 | 10/2000 |

* cited by examiner

APPARATUS AND METHOD FOR DELIVERING A BIOCOMPATIBLE MATERIAL TO A SURGICAL SITE

FIELD OF THE INVENTION

An apparatus and method for surgical procedures, more particularly a minimally invasive apparatus and method for delivering a biocompatible material to a surgical site during various orthopedic procedures.

BACKGROUND OF THE INVENTION

The musculoskeletal system is subject to injury caused by traumatic events as well as by a number of diseases. Repair of connective tissue of the musculoskeletal system is commonly performed. By way of example, articular cartilage is a type of hyaline cartilage that lines the surfaces of the opposing bones in a diarthrodial joint (e.g., knee, hip, shoulder, etc.). Its primary function is to permit smooth, near frictionless movement during articulation between bones of the joint by providing a low-friction interface between the contacting cartilage surfaces of the joint. Articular cartilage is also load bearing, and serves to transmit and distribute compressive joint loads to the underlying subchondral bone.

Articular cartilage is typically damaged in one of two ways, acute trauma suffered through physical activity (such as twisting motion of the leg, sharp lateral motion of the knee, or repetitive impact), or degenerative conditions (such as arthritis or systemic conditions). In addition, as a person ages, articular cartilage loses mechanical strength, rendering the cartilage even more susceptible to trauma. Because articular cartilage tissue is aneural, i.e., having few or no nerves, and avascular, i.e., having few or no blood vessels, the healing of damaged cartilage is limited.

Consequently, various surgical methods are available for the treatment of damaged tissue, such as cartilage. In one treatment approach, the damaged tissue is removed and replaced with natural or synthetic materials that are physiologically acceptable to the human body and which perform the function formerly performed by the material removed. Recently, various orthopedic surgical procedures have replaced native tissue, such as cartilage, with a curable biocompatible material. Such surgical procedures have been performed using minimally invasive techniques, such as arthroscopic and endoscopic techniques, that allow as much of the healthy tissue as possible to remain. One type of biocompatible material that has shown promise for effecting soft tissue repair is hydrogels. Hydrogels are particularly suitable for minimally invasive procedures because they provide controllable phase change, such that the hydrogel may be injected through the minimally invasive device while in a liquid state and then cured in-situ to form a solid or a gel.

While the use of hydrogels has generally been successful to effect joint repair, their use does have some drawbacks. One such drawback is that while the hydrogel is in a liquid form, such as when delivering the hydrogel to a surgical site through the minimally invasive device, it has a relatively low viscosity. Consequently, the hydrogel flows easily and is therefore difficult to contain at the treatment site. Moreover, leakage of the hydrogel into or onto the tissue surrounding the surgical site may not be desirable in some surgical procedures. As a result, the use of hydrogels to effect joint repair has been heretofore limited.

Therefore, there is a need for improvements in a method and apparatus for delivering a biocompatible material to a surgical site.

SUMMARY OF THE INVENTION

Apparatus and method of delivering a biocompatible material to a surgical site that confines the biocompatible material to a desired location at the surgical site. The apparatus and method may also reduce or prevent the leakage of the biocompatible material to the surrounding tissue.

In one embodiment, a device for delivering a curable biocompatible material to a surgical site during a surgical procedure, such as a minimally invasive surgical procedure, includes an elongate cannula having a proximal portion adapted to be located outside a body during the surgical procedure and a distal portion adapted to be located within the body during the surgical procedure and positioned adjacent the surgical site. The elongate cannula includes an outer wall that defines a first interior lumen disposed between the proximal and distal portions and through which the biocompatible material is delivered. The device further includes an initiation member for initiating cross-linking of the biocompatible material while the biocompatible material is within the cannula.

In another embodiment, the initiation member may include a resistive heating element thermally coupled to the outer wall of the cannula. The heating element is adapted to heat at least a portion of the outer wall to thermally initiate cross-linking of the biocompatible material. In such an embodiment, a temperature element may be coupled to the outer wall for measuring a temperature indicative of the temperature of the biocompatible material. The temperature element may, for example, be a thermocouple and be located adjacent the distal portion of the cannula. An outer surface of the outer wall may include an insulating layer to reduce heat transfer to surrounding body tissue when the cannula is positioned within the body. The heating element and the temperature element may be operatively coupled to a controller for controlling the heating element in response to the temperature sensed by the temperature element. In this way, enhanced control of the curing process of the biocompatible material may be achieved. In addition, at least a portion of the outer wall of the cannula may be formed of a material that provides visualization of the biocompatible material through the outer wall.

In another embodiment, the initiation member may include a light source capable of photo initiating cross-linking of the biocompatible material while in the cannula. In this embodiment, the cannula includes an outer wall and a first interior lumen disposed between the proximal and distal portions through which the biocompatible material is delivered to the surgical site. The light source is external to the cannula and may be coupled to a light cannula having a distal portion adjacent the surgical site. Light is transmitted through the light cannula and out of the distal portion. At least a portion of the outer wall is formed of a material capable of transmitting light therethrough and into the first interior lumen to photo initiate cross-linking of the biocompatible material. The light source may be coupled to a controller for controlling the wave length, duration and/or intensity of the light transmitted into the first interior lumen. In this way, enhanced control of the curing process of the biocompatible material may be achieved. Additionally at least a portion of the outer wall of the cannula may be formed of a material that provides visualization of the biocompatible material through the outer wall.

In another embodiment, photo initiation may be used to initiate cross-linking of the biocompatible material while in the cannula. Thus, the initiation member may again include a light source. In this embodiment, the cannula includes an outer wall and a first interior lumen disposed between the proximal and distal portions through which the biocompatible material is delivered to the surgical site. A wall of the first lumen includes a first wall portion formed of a material capable of transmitting light therethrough. The cannula further includes a second interior lumen disposed adjacent the first interior lumen and adapted to transmit light within the second lumen from the light source. A wall of the second lumen includes a second wall portion formed of a material capable of transmitting light therethrough, wherein the first and second wall portions are generally aligned so that light from the second interior lumen may pass through the first and second wall portions to photo initiate cross-linking of the biocompatible material in the first interior lumen. The device may further include a blocking element positioned in either the first or second interior lumen, the blocking element movable between a first position wherein light from the second interior lumen may pass through at least a part of the first and second wall portions and into the first interior lumen, and a second position wherein less light may pass through at least one of the first and second wall portions than in the first position. The device may include a controller operatively coupled to the blocking element to move the blocking element between the first and second positions to thereby control the amount of light transmitted into the first interior lumen. In this way, enhanced control of the curing process of the biocompatible material may be achieved. Additionally, the cannula may include a system for visualizing the surgical site.

A method of delivering a curable biocompatible material to a surgical site in the body includes positioning a distal portion of a cannula adjacent the surgical site and introducing the biocompatible material through a first interior lumen of the cannula. Cross-linking of the biocompatible material is then initiated while the biocompatible material is within the cannula and prior to its delivery to the surgical site. In one embodiment, cross-linking is initiated by heating at least a portion of the cannula. The method may further include monitoring a temperature indicative of the temperature of the biocompatible material and varying heat provided to the portion of the cannula based on the temperature. In another embodiment, cross-linking is initiated by transmitting light through a portion of the outer wall of the cannula and into the first interior lumen to photo initiate cross-linking. In another embodiment, cross-linking is initiated by transmitting light through a second interior lumen of the cannula and transmitting the light from the second interior lumen to the first interior lumen to photo initiate cross-linking of the biocompatible material. The method may further include moving a blocking element between first and second positions to control the amount of light transmitted from the second interior lumen to the first interior lumen.

These and other embodiments will become more readily apparent to those of ordinary skill in the art upon review of the following detailed description taken in conjunction with the accompanying drawings.

BRIEF DESCRIPTION OF THE DRAWING

The accompanying drawings, which are incorporated in and constitute a part of this specification, illustrates embodiments of the invention and, together with a general description of the invention given above, and the detailed description given below, serves to explain the invention.

DETAILED DESCRIPTION

Figure 1:
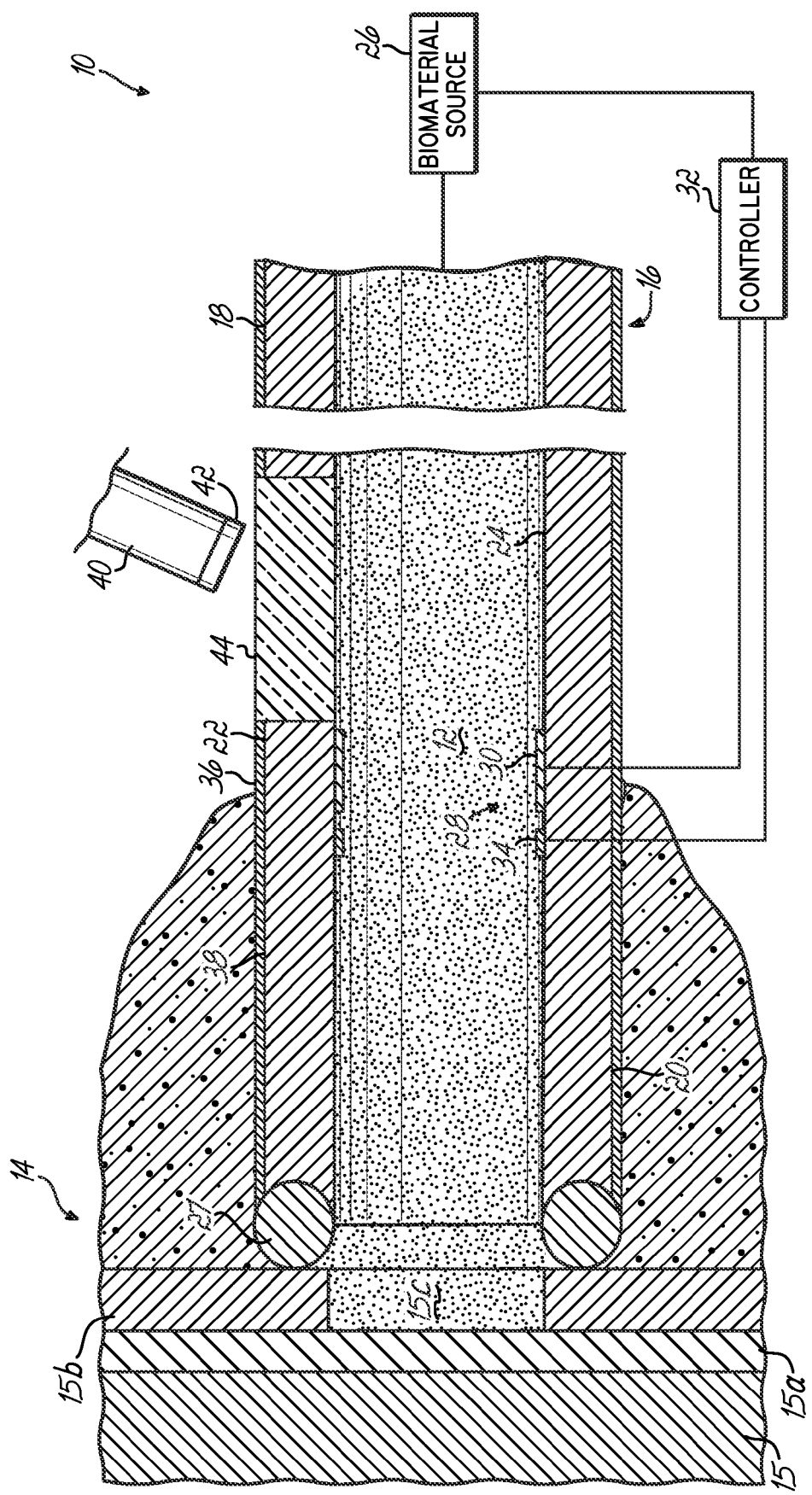
FIG. 1 is a cross-sectional view of an apparatus for delivering a curable biocompatible material to a surgical site in accordance with one embodiment.

Referring to FIG. 1, one embodiment of a device 10 for delivering a curable biocompatible material 12 to a surgical site 14 is schematically illustrated. The device 10 may be used in various surgical procedures, including orthopedic surgical procedures to effect repair of the musculoskeletal system. In one embodiment, the device 10 may be used in minimally invasive procedures, such as arthroscopic and endoscopic procedures, to effect repair of a joint. In one embodiment, the device 10 may be used in orthopedic surgical procedures in general or to repair the cartilage within a diarthrodial joint, such as the knee. By way of example, as shown in FIG. 1, the surgical site 14 may include bone 15, subchondral bone 15a, and cartilage 15b wherein cartilage 15b includes a defect 15c that is to be repaired using embodiments of the invention. The invention, however, is not so limited, as those of ordinary skill in the art will recognize a wide range of surgical applications that may benefit from embodiments of the invention described herein. Thus, embodiments of the invention are not to be limited to orthopedic surgical procedures in general, or to the repair of cartilage in diarthrodial joints in specific.

The device 10 includes an elongate cannula 16 having a proximal portion 18 located outside the body of a patient during a surgical procedure, and a distal portion 20 located within the body of the patient and positioned adjacent the surgical site 14. The device 10 includes an outer wall 22 that defines a first interior lumen 24 disposed between the proximal and distal portions 18, 20 through which the biocompatible material 12 is delivered. The device 10 may include a supply or reservoir 26 of curable biocompatible material in fluid communication with the proximal portion 18 of the cannula 16 to supply the first interior lumen 24 with the biocompatible material 12. As shown in FIG. 1, the end of the cannula may include an elastic seal 27 to reduce or prevent tissue damage as the device 10 is inserted into the body and toward the surgical site 14. In addition, seal 27 may facilitate sealing of the distal portion 20 of cannula 16 with the tissue at the surgical site 14. For example, the tissue surrounding defect 15c may not be smooth but may be rough or irregular. In these applications, the seal 27 may allow the distal portion 20 of the cannula 16 to conform to the irregular contour of the tissue to promote sealing and thus preventing or reducing the leakage of the biocompatible material 12 outside the target area. Moreover, although the distal portion 20 of the cannula 16 is shown as generally straight, the distal portion 20 may have different shapes depending on the application. For example, the distal portion 20 may be semi-circular or otherwise curved to facilitate penetration of the cannula 16 through body tissue and within a joint (not shown).

For minimally invasive procedures, controllable phase change of the biocompatible material may facilitate the delivery of the biocompatible material 12 to the surgical site 14. In particular, in one embodiment, the biocompatible material 12 may be delivered through a portion of the device 10 while in a substantially liquid state and then partially cured within the device prior to delivery of the biocompatible material 12 to the surgical site 14. The controllable phase change of the biocompatible material allows that material to flow through a portion or substantial part of the first interior lumen 24 of the cannula 16 while in a liquid state, but yet be delivered to the surgical site 14 at least partially cured. This may obviate the need for more invasive surgical techniques that may typically be used for locating the biocompatible material 12 at the surgical site 14.

A hydrogel is one such biocompatible material 12 that can exhibit such phase change properties and which may be used in the invention. Cured hydrogels may exhibit physical/chemical characteristics analogous to those of human soft tissue, such as cartilage, and can demonstrate a combination of such properties as load bearing, shear stress resistance, impact absorption, and/or wear characteristics. The term hydrogel includes liquid and/or semi-solid long chain hydrophilic molecules that form cavities or spaces that contain entrapped liquids, typically water, at a concentration ranging from about 20% to about 95%. The cavities absorb water (or other liquids) from the surrounding environment, and can slowly release the water as the molecules biodegrade or experience localized changes in load bearing.

Hydrogels may be classified according to composition (homopolymer, copolymer, multipolymer, or interpenetrating hydrogels), ionic charge (neutral, anionic, cationic, or ampholytic hydrogels), and/or structure (amorphous, semicrystalline, or hydrogen-bonded hydrogels). Methods, components, concentrations, conditions, etc. to produce hydrogels are known by one skilled in the art such as described in U.S. Pat. Nos. 6,949,590; 6,511,650; 6,497,902; Published U.S. patent application No. 20060252159; and Hoffman (Advanced Drug Delivery Reviews, Vol. 43, 2002, pp 3-12) each of which are incorporated herein by reference in its entirety.

Hydrogels may be prepared from natural polymers that include, but are not limited to, collagen, hyaluronate, chitosan, gelatin, algenate, pectin, carrageenen, chondroiten sulfate, dextran sulfate, polylysine, carboxymethyl chitin, fibrin, dextran, agarose, and pullulan. Hydrogels also may be prepared from synthetic polymers that include, but are not limited to, poly(2-hydroxyethylmethacrylate (HEMA), polyphazene, poly(ethylene oxide) PEO and its copolymers, polyesters such as PEG (polyethylene glycol)-PLA (polylactic acid)-PEG, PEG-PLGA-PEG, PEG-PCL (polycaprolactone)-PEG, PLA-PEG-PLA, PHB (poly(3-hydroxybutyrate)), P(PF-co-EG) plus or minus acrylate end groups, P(PER/PBO terephthalate), other polymers such as PEG-bis-PLA-acrylate), PEG-g-P(Aam-co-Vamine), PAAm, P(NIPAAm-co-Aac), P(NIPAAm-co-EMA), PVAc/PVA, PNVP, P(MMA-co-HEMA), P(AN-co-allyl sulfonate), P(biscarboxy-phenoxy-phosphazine), P(GEMA-sulfate). Hydrogels may be prepared from both natural and synthetic polymers, examples of which include, but are not limited to, P(PEG-co-peptides), alginate-g-(PEO-PPO-P EO), P(PLGA-co-serine), collagen-acrylate, alginate-acrylate, P(HPMA-g-peptide), P(hema/Matrigel®), and HA-g-NIPAAm.

Hydrogels may be prepared from branched deoxyribonucleic acid (DNA) that self-forms into various shapes (e.g., a cross, a "Y", a "T"). These may have non-base paired termini to which a complementary sequence may anneal (i.e., "sticky ends"). These may be used with ligases to link DNA strands to each (e.g., Steele, B. Sep. 28, 2006, Cornell CHRONICLE, page 7). Cross-shaped branched DNA forms a gel by linking into sheets of tiny squares that tangle in three dimensions; Y shapes form hexagonal structures like a chain link fence that combine into a fibrous three-dimensional form; T shapes create random, disorganized patterns that resemble scales, etc. Properties such as rigidity and/or absorbance of the resulting hydrogels may be altered by adjusting the types of branched DNA used and the DNA concentration.

In one embodiment, hydrogels are long-chain molecules cross-linked to one another. In another embodiment, hydrogels are long-chain molecules that are not cross-linked; while these are able to absorb liquids within their cavities, they are not soluble due to the presence of hydrophobic and hydrophilic regions in their structure. The term hydrogel is also applied to hydrophilic polymers in a dry state (xerogel).

Cross-linking may be effected by physical, chemical, and/or photo cross-linking. Physical cross-linking occurs due to ionic linkages, hydrogen bonding, van der Waals forces, or other physical forces. Chemical cross-linking occurs due to formation of covalent linkages using chemical initiators. Photo cross-linking, also termed photopolymerization, of hydrogels may occur by exposure to ultraviolet and/or visible light, either in the presence or absence of a photo initiator. Examples of polymers and methods of use are described in U.S. Pat. Nos. 5,567,435 and 6,156,478; and Published U.S. patent application No. 20060252159. Examples of polymers/monomers suitable to form ionically cross-linked hydrogels with adjustable gellation times are disclosed in U.S. Pat. No. 6,497,902. Examples of polymers suitable to form porous hydrogels are disclosed in U.S. Pat. No. 6,511,650. Examples of polymers suitable to form bioabsorbable polymer hydrogels for sustained release of drugs are disclosed in Published U.S. patent application No. 2006/0251719.

Hydrogels may contain both hydrophobic and hydrophilic components. Preparation of these hydrogels does not rely on use of copolymers or physical blending, but instead relies on hydrophobic and hydrophilic components. These components are convertible into a one phase cross-linked polymer network structure by free radical polymerization, as described in U.S. patent application Publication No. U.S. 2002/0161169.

Hydrogels may be formulated as temperature sensitive compounds, described in U.S. patent application Publication No. U.S. 2006/0188583. Polymers, either commercially available or synthesized, are dissolved in water or other liquid, and an agent that facilitates cross-linking such as sodium hyaluronate (SH) is added. The temperature sensitive hydrogel are liquid at about ambient room temperature (about 20° C.) and transition to become a solid (gel) at about body temperature (about 37° C.). Any polymers may be used to prepare temperature sensitive hydrogels as long as it possess the necessary properties to support the hydrogel. Examples of such polymers include, but are not limited to, N-isopropyl acrylamide polymer, ethylhydroxyethylcellulose and its derivatives, poly(ethylene glycol)/poly(D,L-lactic acid-co-glycolic acid) block co-polymers and analogs, and poly (etheylene oxide-b-propylene oxide-b-ethylene oxide) (Poloxamers or PLURONICS® polymers, which are block copolymers of the type ABA, consisting of a central, hydrophobic block of polypropylene oxide, which is edged by two hydrophilic blocks of polyethylene oxide. The polymers are derived from the sequential polymerization of propylene oxide and ethylene oxide).

Hydrogels may be polymerized in-situ. U.S. Published Patent Application No. 2006/018894 describes in-situ polymerization of a hydrogel using UV light in the presence of stratum corneum tissue. U.S. Published Patent Application No. 2004/0241203 describes a fluid composition comprising particulate material, and a cross-linking agent, the particles cross-linking to form a matrix on introduction to the cross-linking agent in or on a target tissue. Changing the amount of monomer and cross-linker can change the thickness and pore size of hydrogel layers as described in PCT application WO 00/66265.

Hydrogels may serve as an extracellular matrix (ECM), or bioscaffold, to provide a surface upon which cells can attach. This may have applications in tissue engineering implantation. As one example, Schmedlen et al (Biomaterials 23 (2002) 4325) describe polyvinyl alcohol hydrogels that can be modified with cell adhesion peptides. As another example, Khademhosseini et al. describe gradient hydrogels embedded with the peptide Arg-Gly-Asp (RGD) that can bind cell integrins (membrane bound receptors). Published U.S. patent application No. 2006/0233850 discloses bioscaffolds formed of hydrogels that are cross-linked in-situ in an infarcted region of the heart.

Hydrogels may serve as drug delivery devices. In one embodiment, a hydrogel may gradually dispense a drug or other liquid within its cavities (e.g., U.S. patent application Publication No. 2006/0251719 discloses a sustained-release, bioabsorbable polymer hydrogel drug preparation). Such hydrogels form a complex with the drug through physiochemical interactions to effect sustained drug release, in effect forming a microcapsule. Techniques for preparing, loading, etc. such hydrogels are known to one skilled in the art.

The invention, however, is not limited to hydrogels, as those of ordinary skill in the art will recognize other suitable biocompatible materials capable of being delivered to the surgical site by means of a cannula, and cured to form a replacement material during a surgical procedure.

As noted above, however, the biocompatible material 12, such as a hydrogel, may exhibit a relatively low viscosity when in the liquid state. The biocompatible material 12 then flows easily and thus passes through the cannula 16 with reduced resistance to flow and with a relatively small pressure gradient. While this may be desirable to facilitate delivery of the biocompatible material 12 through the device 10, the relatively low viscosity may make confining the biocompatible material 12 to a desired target area of the surgical site 14 challenging. In other words, the enhanced flowability of the biocompatible material 12 may allow the material to essentially leak into or onto the tissue surrounding the surgical site 14 or other areas where no biocompatible material is desired. Consequently, measures may be taken to confine the biocompatible material 12 at a desired target area of the surgical site 14. For example, commonly assigned U.S. application Ser. No. 11/613,319, filed on Dec. 20, 2006, titled "Apparatus for Deliverying a Biocompatible Material to a Surgical Site and Method of Using the Same," discloses using an expandable confinement member at the distal portion of the cannula to confine the biocompatible material to the desired target area of the surgical site. Embodiments of the invention disclosed herein provide an alternate approach to preventing the biocompatible material from leaking into or onto the surrounding tissue at the surgical site.

To address the flowability of the biocompatible material 12 at the surgical site 14, the device 10 may further include an initiation member 28 for initiating cross-linking of the biocompatible material 12 while the biocompatible material 12 is within the device 10. Initiating cross-linking of the biocompatible material 12 initiates curing and results in an increase in the viscosity of the biocompatible material 12 so that the flowability of the biocompatible material 12 is reduced prior to its delivery to the surgical site 14. As illustrated in FIG. 1, in one embodiment the initiation member 28 may be configured as a heating element 30 for thermally initiating cross-linking of the biocompatible material 12 within cannula 16. For example, the heating element 30 may be a resistive heating wire or coil, as is known in the art. In one embodiment, the heating element 30 is thermally coupled to the outer wall 22 of the cannula 16 for heating at least a portion of the outer wall 22. The biocompatible material 12 may be in direct contact with the heated portion of the outer wall 22 or at least is thermally coupled to the outer wall 22, such as by high thermal conductivity materials (not shown), so that heat from the heating element 30 is transferred to the biocompatible material 12 to cause thermal initiation of the biocompatible material 12. The heating element 30 may be appropriately located along the cannula 16 such that the viscosity of the biocompatible material 12 is generally in a desired range when the biocompatible material 12 reaches the end of the cannula 16 and is delivered to the surgical site 14. The viscosity range may be selected so as to retain the partially cured biocompatible material 12 within the desired target area of the surgical site 14. Once delivered to the surgical site 14, the curing process is completed in-situ to form a solid or gelled implant.

The viscosity of the biocompatible material 12 adjacent the end of the cannula 16 depends on several factors, including not only the location of the heating element 30 along the cannula 16 but also the amount of heating of the biocompatible material 12 by the heating element 30. To provide enhanced control of the curing process of the biocompatible material 12, device 10 may include a controller 32 operatively coupled to the heating element 30 and capable of controlling the amount of heat generated by heating element 30 (i.e., the amount and/or duration of heating). Device 10 may further include a temperature element 34 thermally coupled to the outer wall 22 and adapted to measure a temperature indicative of the temperature of the biocompatible material 12 in first interior lumen 24. For example, the temperature element 34 may be located adjacent the distal portion 20 of the cannula 16 so as to indicate the temperature of the biocompatible material 12 adjacent the end of the cannula 16. The temperature element 34 may, for example, be a thermocouple, thermistor, or other temperature sensing device known to those of ordinary skill in the art. The temperature element 34 is also operatively coupled to controller 32 so as to control heating element 30 in response to the temperature sensed by the temperature element 34. In this way, the curing process of the biocompatible material 12 may be controlled so as to deliver the biocompatible material 12 to the surgical site 14 at a viscosity sufficient to reduce or eliminate leakage of the biocompatible material 12 into or onto the tissue surrounding the surgical site 14. Moreover, the controller 32 may also be operatively coupled to the reservoir 26 so as to supply the biocompatible material 12 to the first interior lumen 24 at a predetermined rate or volume, which also factors in determining the viscosity of the biocompatible material 12 at the end of the cannula 16. For example, the controller 32 may supply biocompatible material 12 to first interior lumen 24 at a linear rate of about 1 µm/sec to about 10 cm/sec or a volumetric flow rate of about 0.1 µl/sec to about 1.0 ml/sec.

Because this embodiment uses thermal initiation to cross-link the biocompatible material 12, it may be desirable to reduce the effects of heating from heating element 30 on the surrounding body tissue. To this end, the device 10 may include an insulating coating or layer 36 on the outer surface 38 of the outer wall 22 of cannula 16 at least along a portion thereof. In particular, the insulating coating 36 is located adjacent the heating element 30. Insulating layer 36 not only reduces the heat transfer to the surrounding body tissue when the cannula 16 is positioned within the body, but layer 36 also focuses the thermal energy from the heating element 30 to the biocompatible material 12, thus enhancing the thermally initiated cross-linking of the biocompatible material 12.

In another embodiment, the device 10 may include a second cannula 40 inserted into the body of the patient such that its distal portion 42 is positioned adjacent the surgical site 14. The second cannula 40 carries optical instrumentation as is known in the art for viewing the biocompatible material 12 within the cannula 16. To this end, at least a portion 44 of the outer wall 22 is formed of a material that provides for visualization of the biocompatible material 12 through the outer wall 22.

Figure 2:
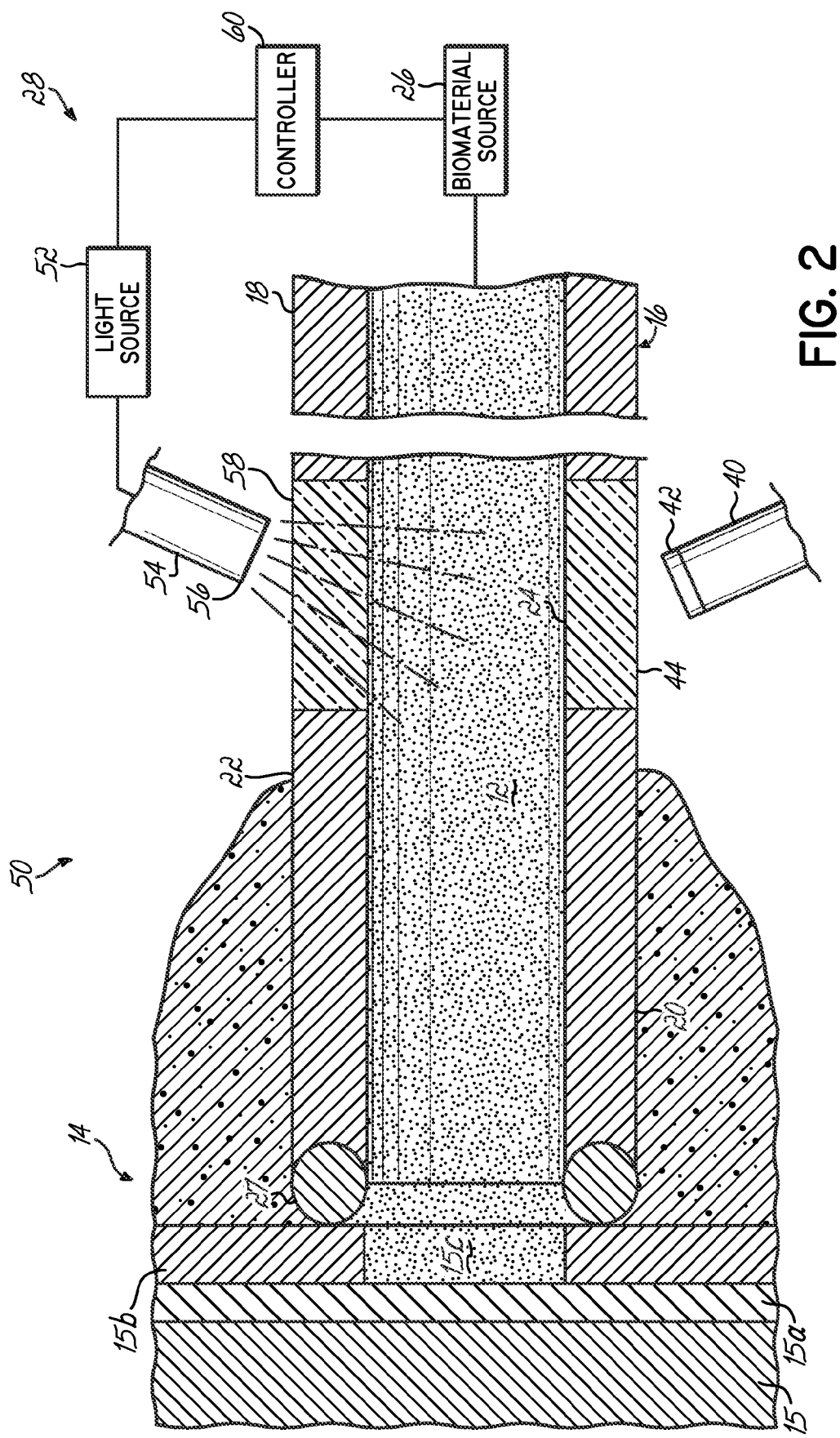
FIG. 2 is a cross-sectional view of an apparatus for delivering a curable biocompatible material to a surgical site in accordance with another embodiment.

FIG. 2, in which like reference numerals refer to like features in FIG. 1, illustrates another embodiment of a device 50 for delivering a curable biocompatible material 12 to a surgical site 14. The device 50 includes an elongate cannula 16 having a proximal portion 18 located outside the body of a patient during a surgical procedure, and a distal portion 20 located within the body of the patient and positioned adjacent the surgical site 14. The device 50 includes an outer wall 22 that defines a first interior lumen 24 disposed between the proximal and distal portions 18, 20 through which the biocompatible material 12 is delivered. The device 50 may include a supply or reservoir 26 of curable biocompatible material in fluid communication with the proximal portion 18 of the cannula 16 to supply the first interior lumen 24 with the biocompatible material 12.

In this embodiment, initiation of cross-linking of the biocompatible material 12 is achieved through photo initiation. Thus, the initiation member 28 may be configured as a light source 52 for generating light sufficient to photo initiate cross-linking of the biocompatible material 12. To this end, device 50 may include a light cannula 54 that is inserted into the body of the patient such that its distal portion 56 is positioned adjacent the surgical site 14. The light cannula 54 is coupled to light source 52 and is capable of transmitting light out of the distal portion 56 of cannula 54. In one embodiment, the light source 52 may be a fiber optic bundle positioned within light cannula 54 and adjacent distal portion 56. Alternately, the light source 52 may be positioned away from the distal portion 56 of the cannula 54 and light channeled through the cannula 54 so as to be transmitted from the end of the cannula 54. Those of ordinary skill in the art will recognize other light sources that may be used in embodiments of the invention. Moreover, at least a portion 58 of the outer wall 22 of cannula 16 is formed of a material capable of transmitting light therethrough. Thus, light from light cannula 54 passes through the portion 58 of outer wall 22 and into first interior lumen 24 to photo initiate cross-linking of the biocompatible material 12. Although only one light cannula is shown in FIG. 2, device 50 may include multiple light cannulas, which may, for example, be circumferentially spaced about the periphery of cannula 16 so as to transmit light into first interior lumen 24. The use of multiple light cannulas may provide a more homogeneous polymerization of the biocompatible material 12 in first interior lumen 24.

The viscosity of the biocompatible material 12 adjacent the end of the cannula 16 depends on several factors, including the wave length, duration and/or intensity of the light from light source 52, as well as the size and location of the portion 58 of the outer wall 22 through which the light is transmitted. These parameters may be varied to control the curing process of the biocompatible material 12 within the cannula 16. In one embodiment, the light source 52 may be operatively coupled to a controller 60 for controlling the light generated by the light source 52. In addition, the portion 58 of the outer wall 22 through which the light passes may be positioned along the cannula 16 and sized such that the viscosity of the biocompatible material 12 is generally in a desired range when the biocompatible material 12 reaches the end of the cannula 16. For example, the portion 58 may have a length from about 1 mm to about 10 cm. In this way, the curing process may be controlled to deliver the biocompatible material 12 to the surgical site 14 at a viscosity sufficient to reduce or eliminate leakage of the biocompatible material 12 into or onto the tissue surrounding the surgical site 14.

The controller 60 may also be operatively coupled to the reservoir 26 to supply the biocompatible material 12 to the first interior lumen 24 at a predetermined rate or volume, which also factors in determining the viscosity of the biocompatible material 12 at the end of the cannula 16. For example, the controller 60 may supply biocompatible material 12 to first interior lumen 24 at a linear rate of about 1 µm/sec to about 10 cm/sec or a volumetric flow rate of about 0.1 µl/sec to about 1.0 ml/sec. The biocompatible material 12 may be configured such that visible light and/or ultraviolet light initiates cross-linking. Accordingly, the light source 52 may be configured to generate visible and/or ultraviolet light as required by the specific application or cross-linking system. This embodiment may also include a second cannula 40 for viewing the biocompatible material 12 within the cannula 16. Accordingly, at least a portion 44 of the outer wall 22 is formed of a material that provides for visualization of the biocompatible material 12 through the outer wall 22.

Figure 3:
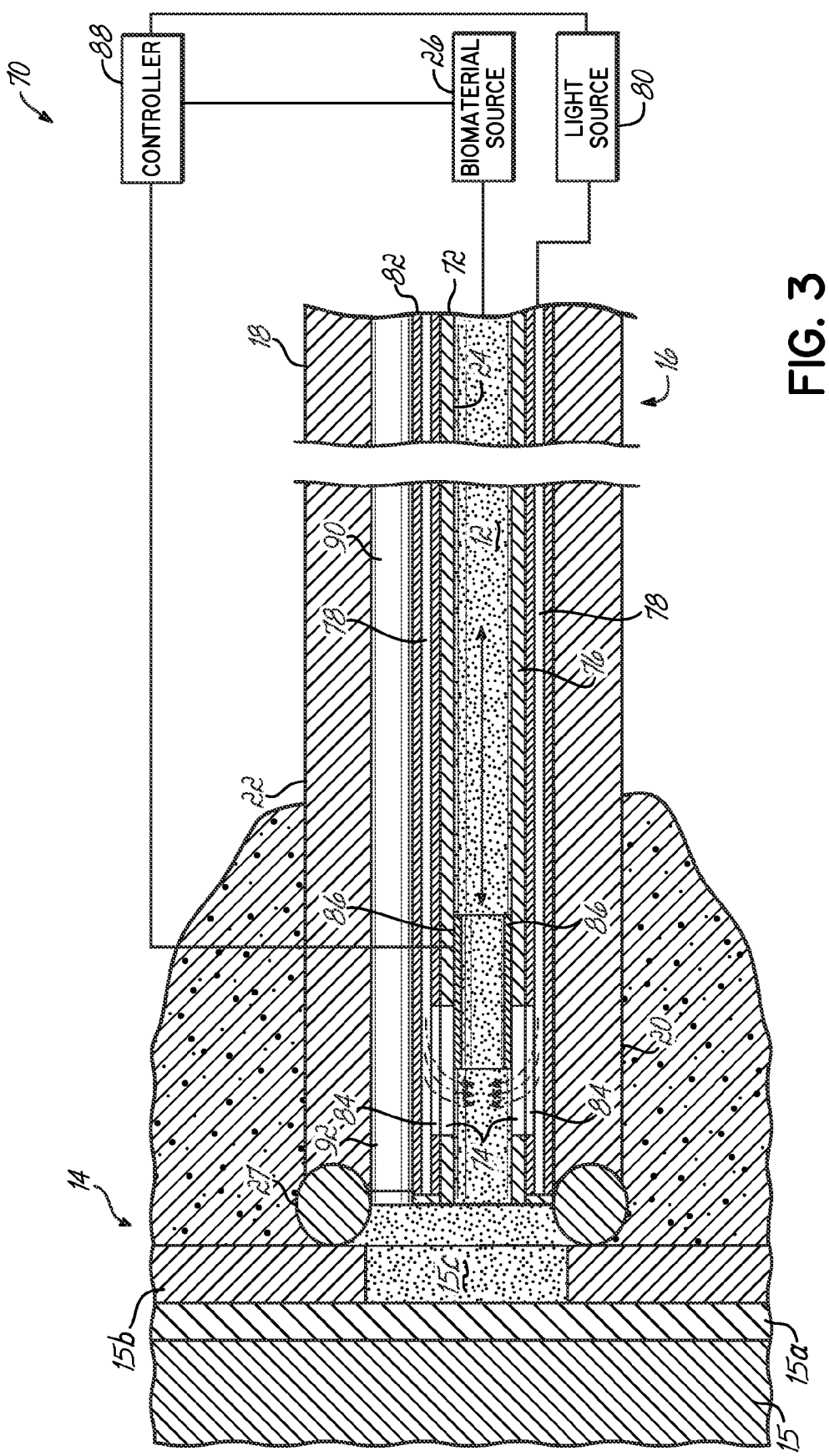
FIG. 3 is a cross-sectional view of an apparatus for delivering a curable biocompatible material to a surgical site in accordance with another embodiment.

FIG. 3, in which like reference numerals refer to like features in FIG. 1, illustrates another embodiment of a device 70 for delivering a curable biocompatible material 12 to a surgical site 14. The device 70 includes an elongate cannula 16 having a proximal portion 18 located outside the body of a patient during a surgical procedure, and a distal portion 20 located within the body of the patient and adjacent the surgical site 14. The device 70 includes an outer wall 22 and a first interior lumen 24 disposed between the proximal and distal portions 18, 20 through which the biocompatible material 12 is delivered. The device 70 may include a supply or reservoir 26 of curable biocompatible material in fluid communication with the proximal portion 18 of the cannula 16 to supply the first interior lumen 24 with the biocompatible material 12. The first interior lumen 24 is defined by a wall 72 having a first wall portion 74 formed of a material capable of transmitting light therethrough. In one embodiment, the first wall portion 74 is along a distal portion 76 of wall 72 that forms first interior lumen 24.

The device 70 further includes a second interior lumen 78 disposed between the proximal and distal ends 18, 20 of cannula 16 and is adapted to transmit light therethrough from a light source 80 operatively coupled to second interior lumen 78. The second interior lumen 78 is defined by a wall 82 having a second wall portion 84 formed of a material capable of transmitting light therethrough. The first and second wall portions 74, 84 are generally aligned with each other so that light from second interior lumen 78 may pass through the first and second wall portions 74, 84 and into the first interior lumen 24 to photo initiate cross-linking of the biocompatible material 12 contained therein. In one embodiment, the light source 80 may be a fiber optic bundle positioned within the second lumen 78 such that the light source 80 is adjacent the second wall portion 84. Alternately, the light source 80 may be positioned away from the second wall portion 84 and the light channeled through the second interior lumen 84 and into the first interior lumen 24 via the first and second wall portions 74, 84. In one embodiment, the first and second wall portions 74, 84 are substantially equal in length. The wall portions 74, 84 may be between about 1 mm to about 10 cm. The biocompatible material 12 may be configured such that visible and/or ultraviolet light initiates cross-linking. Accordingly, the light source 80 may be configured to generate visible and/or ultraviolet light as required by the specific application or cross-linking system. As shown in FIG. 3, the device 70 may include multiple lumens (two shown) for introducing light into the first interior lumen 24, as dictated by the specific application. Furthermore, in this embodiment, the outer wall 22 may be formed from an opaque or other material to protect body tissue from light exposure.

To provide control of the curing process of the biocompatible material 12, the device 70 may further include a blocking element 86 in either the first or second interior lumens 24, 78. The blocking element 86 is adapted to control the amount of light from the second interior lumen 78 that passes through the first or second wall portions 74, 84 and into the first interior lumen 24. For example, as shown in FIG. 3, the first interior lumen 24 may include the blocking element 86. Alternately, the second interior lumen 78 may include the blocking element 86 (not shown). In any embodiment, the blocking element 86 is movable between a first position wherein light from the second interior lumen 78 passes through at least a part of the first and second wall portions 74, 84 and into the first interior lumen 24, and a second position wherein less light passes through at least a portion of the first and second wall portions 74, 84 and into the first interior lumen 24. For example, the blocking element 86 may have a position that exposes the entire first and second wall portions 74, 84. The blocking element 86 may also have a position that completely closes off the first and second wall portions 74, 84 and prevents any light to pass therethrough. Additionally, the blocking element 86 may include a position that partially closes off the second wall portion 84, as shown in FIG. 3. The movement of the blocking element 86 between the first and second positions controls the amount of light that passes into the first interior lumen 24 and therefore provides some control of the curing process of the biocompatible material 12 within first interior lumen 24.

In one embodiment, the device 70 includes a controller 88 that is operatively coupled to the blocking element 86 for moving the blocking element 86 between the first and second positions. The controller 88 may also be operatively coupled to the light source 80 to control the wave length, duration and/or intensity of the light generated by light source 80. In this way, the light source 80 and blocking element 86 may be controlled such that the viscosity of the biocompatible material 12 is generally in a desired range when the biocompatible material 12 reaches the end of the cannula 16 and is delivered to the surgical site 14. The controller 88 may also be operatively coupled to the reservoir 26 so as to supply the biocompatible material 12 to the first interior lumen 24 at a predetermined rate or volume, which also factors in determining the viscosity of the biocompatible material 12 at the end of the cannula 16. The controller is capable of varying the rate at which the biocompatible material flows through the cannula. For example, the controller 88 may supply biocompatible material 12 to first interior lumen 24 at a linear rate of about 1 μm/sec to about 10 cm/sec or a volumetric flow rate of about 0.1 μl/sec to about 1.0 ml/sec.

In another embodiment, the device 70 further includes a visualization system for viewing the surgical site 14. In such an embodiment, device 70 may include a cannula 90 carried within cannula 16 having a distal portion 92 positioned adjacent the surgical site 14. The cannula 90 carries optical instrumentation for viewing the surgical site 14, as is generally known in the art. As recognized by those of ordinary skill in the art, the cannula 90 may alternately be positioned external to the cannula 16 for viewing the surgical site 14, such as that shown in FIGS. 1 and 2.

In use, after the surgical site 14 has been prepared, such as by aspiration of fluid at the surgical site 14 and/or contouring the underlying tissue as dictated by the specific application, the cannula 16 is inserted into the body of a patient and advanced so that its distal portion 20 is proximate the surgical site 14. Biocompatible material 12 is then introduced through the first interior lumen 24. Along a portion of the length of the cannula 16, the biocompatible material 12 is in a substantially liquid state with a low viscosity that facilitates its delivery through the first interior lumen 24 of cannula 16. Prior to being delivered to the surgical site 14, however, cross-linking of the biocompatible material 12 is initiated while the biocompatible material 12 is within the cannula 16. Initiating cross-linking of the biocompatible material 12 initiates curing and therefore increases the viscosity of the biocompatible material 12 prior to its delivery to the surgical site 14. With the viscosity increased, biocompatible material 12 does not flow as readily and the biocompatible material 12 is retained or confined in the desired target area of the surgical site 14. Therefore, the leakage of the biocompatible material 12 into or onto the surrounding tissue at the surgical site 14 is reduced or prevented.

Initiation of cross-linking to cause curing may occur in several ways including thermal, chemical, and photo initiation. By way of example, the embodiment shown and described in FIG. 1 utilizes thermal initiation by heating at least a portion of the cannula 16. In this embodiment, control of the curing process may be achieved by monitoring the temperature of the biocompatible material 12 using temperature element 34 and varying the heating of heating element 30 based on the temperature of the biocompatible material 12. Alternately, and as shown and described in FIGS. 2 and 3, photo initiation may be used to initiate cross-linking of the biocompatible material 12. As shown in FIG. 2, light may be transmitted through at least a portion 58 of the outer wall 22 and into the first interior lumen 24 to photo initiate cross-linking of the biocompatible material 12 therein. Moreover, as shown in FIG. 3, light may be transmitted through a second interior lumen 78 in the cannula 16 and this light transmitted into the first interior lumen 24 to photo initiate the biocompatible material 12 therein. In these embodiments, the curing process of the biocompatible material 12 may be controlled by controlling the amount of light transmitted to the first interior lumen 24. For example, in the embodiment shown in FIG. 2, the intensity of the light source 52 may be controlled by controller 60. Additionally, in the embodiment shown in FIG. 3, the blocking element 86 may be moved between first and second positions by controller 88 to control the amount of light transmitted from the second interior lumen 78 to the first interior lumen 24. By controlling the amount of heating (thermal initiation) and the amount of light (photo initiation) that passes into the biocompatible material, the viscosity of the biocompatible material at the end of the cannula may have a desired range sufficient to reduce or eliminate leakage of the biocompatible material into or onto the tissue surrounding the surgical site.

While the present invention has been illustrated by a description of various preferred embodiments and while these embodiments have been described in some detail, it is not the intention of the inventors to restrict or in any way limit the scope of the appended claims to such detail. Additional advantages and modifications will readily appear to those skilled in the art. The various features of the invention may be used alone or in numerous combinations depending on the needs and preferences of the user.

What is claimed is:

1. A device, comprising: an elongate cannula having a proximal portion adapted to be located outside a body during a surgical procedure, and a distal portion adapted to be located within the body during the surgical procedure and adjacent a surgical site to which a curable biocompatible material is to be delivered, the cannula comprising: an outer wall; a first interior lumen disposed between the proximal and distal portions through which the biocompatible material is delivered, a wall of the first lumen including a first wall portion capable of transmitting light therethrough; a second interior lumen disposed adjacent the first interior lumen and adapted to transmit light within the second lumen, a wall of the second lumen including a second wall portion capable of transmitting light therethrough, the first and second wall portions being generally aligned so that light from the second lumen may pass through the first and second wall portions to photo initiate cross-linking of the biocompatible material in the first lumen; a blocking element positioned in at least one of the first or second lumens and movable between a first position wherein light from the second lumen may pass through at least a part of the first and second wall portions to the first lumen, and a second position wherein less light may pass through at least one of the first and second wall portions than in the first position; and an end of the cannula to be located adjacent a surgical site.

2. The device of claim 1, further comprising: a fiber optic bundle positioned in the second lumen for generating light to be transmitted within the second lumen, the fiber optic cable terminating proximal the second wall portion.

3. The device of claim 1, further comprising: a light source for generating light to be transmitted within the second lumen.

4. The device of claim 3, wherein the light source is selected from the group consisting of a visible and an ultraviolet light source.

5. The device of claim 1, wherein the outer wall is opaque to protect body tissue from light exposure.

6. The device of claim 1, further comprising: a controller adapted to move the blocking element between the first and second positions and control the amount of light transmitted through the first and second wall portions.

7. The device of claim 6, wherein the controller is coupled to a supply of the biocompatible material and capable of varying the rate at which the biocompatible material flows through the cannula.

8. A method of delivering a curable biocompatible material to a surgical site in the body, comprising: positioning a distal portion of a cannula adjacent the surgical site; introducing the biocompatible material through a first lumen of the cannula; and initiating cross-linking of the biocompatible material prior to delivery to the surgical site while the biocompatible material is within the cannula, wherein initiating cross-linking comprises: transmitting light through a second lumen of the cannula to the first lumen to photo initiate cross-linking of the biocompatible material; and moving a blocking element between a first and a second position to control the amount of light transmitted from the second lumen to the first lumen.

9. The method of claim 8, wherein light is transmitted by a fiber optic bundle positioned in the second lumen of the cannula.

10. The method of claim 8, further comprising: controlling wherein light transmitted from the second lumen is selected from the group consisting of visible and ultraviolet light.

11. The method of claim 8, further comprising: protecting body tissue from exposure to light transmitted from the second lumen to the first lumen.

12. The method of claim 11, wherein at least a portion of the cannula is opaque.

13. The method of claim 8, wherein the blocking element is moved by a controller.

14. The method of claim 13, wherein the controller is coupled to a supply of the biocompatible material and capable of varying the rate at which the biocompatible material flows through the cannula.

* * * * *

UNITED STATES PATENT AND TRADEMARK OFFICE
CERTIFICATE OF CORRECTION

| | | |
|---|---|---|
| PATENT NO. | : 7,720,533 B2 | Page 1 of 1 |
| APPLICATION NO. | : 11/613456 | |
| DATED | : May 18, 2010 | |
| INVENTOR(S) | : Behravesh et al. | |

It is certified that error appears in the above-identified patent and that said Letters Patent is hereby corrected as shown below:

On the title page, under (73) Assignee, delete "Orthobiologicals" and insert --Orthobiologics--.

Column 14, Claim 10, Line 22, delete "further comprising: controlling".

Signed and Sealed this
Twenty-eighth Day of December, 2010

David J. Kappos
*Director of the United States Patent and Trademark Office*